United States Patent [19]

Brown

[11] 4,388,317

[45] Jun. 14, 1983

[54] PYRIMIDONES HAVING HISTAMINE H₂-ANTAGONIST ACTIVITY

[75] Inventor: Thomas H. Brown, Tewin, England

[73] Assignee: Smith Kline & French Laboratories Limited, Welwyn Garden City, England

[21] Appl. No.: 248,096

[22] Filed: Mar. 27, 1981

[51] Int. Cl.³ ............... A61K 31/505; C07D 239/24
[52] U.S. Cl. ................... 424/248.51; 424/248.5; 424/248.56; 424/251; 544/82; 544/123; 544/331
[58] Field of Search ............. 424/270, 251, 248.51, 424/248.56, 248.5; 544/331, 82, 123

[56] References Cited

U.S. PATENT DOCUMENTS

| | | | |
|---|---|---|---|
| 4,154,834 | 5/1979 | Brown et al. | 424/270 |
| 4,218,452 | 8/1980 | Brown et al. | 424/270 |
| 4,234,588 | 11/1980 | Brown et al. | 424/270 |
| 4,255,440 | 3/1981 | Once et al. | 424/248.5 |

OTHER PUBLICATIONS

Derwent Abstract 38240C (WP 8000966).
Derwent Abstract 64650C (EP 15138).

*Primary Examiner*—Nicholas S. Rizzo
*Attorney, Agent, or Firm*—Joan S. Keps; Richard D. Foggio; Alan D. Lourie

[57] ABSTRACT

The compounds of this invention are 5-[dialkylaminoalkylfuranyl (or thienyl, phenyl or pyridyl)]-4-pyrimidones having histamine H₂-antagonist activity. A specific compound of this invention is 2-[2-(5-dimethylaminomethyl-2-furanylmethylthio)ethylamino]-5-(5-dimethylaminomethyl-2-furanylmethyl)-4-pyrimidone.

30 Claims, No Drawings

PYRIMIDONES HAVING HISTAMINE H₂-ANTAGONIST ACTIVITY

This invention relates to pyrimidone derivatives, pharmaceutical compositions containing them and methods of blocking histamine H$_2$-receptors by administering these compounds.

Histamine, a physiologically active compound endogenous in mammals, exerts its action by interacting with certain sites called receptors. One type of receptor is known as a histamine H$_1$-receptor (Ash and Schild, Brit. J. Pharmac 1966, 27, 427) and the actions of histamine mediated through these receptors are blocked by drugs commonly called "antihistamines" (histamine H$_1$-antagonists) a common example of which is mepyramine. A second type of histamine receptor is known as the H$_2$-receptor (Black et al. Nature 1972, 236, 385). These receptors are not blocked by mepyramine but are blocked by burimamide. Compounds which block these histamine H$_2$-receptors are called histamine H$_2$-antagonists.

Histamine H$_2$-antagonists are useful in treating disease conditions caused by the biological effects of histamine mediated through H$_2$-receptors, for example, as inhibitors of gastric acid secretion, in the treatment of inflammation mediated through histamine H$_2$-receptors and as agents which act on the cardiovascular system, for example, as inhibitors of effects of histamine on blood pressure mediated through histamine H$_2$-receptors.

Cimetidine is an example of a histamine H$_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine 1- and H$_2$-receptors and blockade of both types of receptors is useful in managing such conditions. These conditions include inflammation mediated by histamine, for example skin inflammation, and those hypersensitivity responses due to the action of histamine at H$_1$- and H$_2$-receptors, for example allergies.

A class of pyrimidone derivatives has now been discovered which are particularly active as histamine H$_2$-antagonists.

Accordingly, the present invention provides compounds of formula (I):

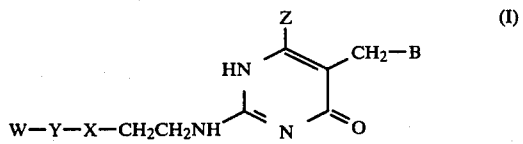

where W is a 2-furanyl or 2-thienyl group optionally substituted in the 5-position with a group $R^1R^2N(CH_2)_m-$; a phenyl group substituted in the 3- or 4-position with a group $R^1R^2N(CH_2)_m-$; a 4-imidazolyl group optionally substituted in the 5-position with methyl or bromine; a 2-pyridyl group optionally substituted in the 3-position with $C_{1-4}$ alkyl, $C_{1-4}$ alkoxy, halogen, amino or hydroxy; a 2-thiazolyl group or a 2-guanidino-4-thiazolyl group; X is methylene or sulphur and Y is methylene or, provided X is methylene and W is a substituted phenyl group, oxygen; Z is hydrogen or $C_{1-4}$ alkyl; and B is a 2-furanyl or 2-thienyl group substituted in the 5-position by a group $R^1R^2N(CH_2)_m-$; a phenyl group substituted in the 3- or 4-position by a group $R^1R^2N(CH_2)_m-$ or a 3-pyridyl group substituted in position 5 or 6 or a 4-pyridyl group substituted in position 2 or a 2-pyridyl group substituted in position 4 or 5 by a group $R^1R^2N(CH_2)_m$; $R^1$ and $R^2$ are $C_{1-4}$ alkyl or together with the nitrogen atom to which they are attached form a pyrrolidino, piperidino or morpholino group; m is 1 to 4; and pharmaceutically acceptable acid addition salt thereof.

By way of example Z can be hydrogen, methyl, ethyl, n-propyl or n-butyl but preferably Z is hydrogen.

With reference to B examples of $C_{1-4}$ alkyl groups which $R^1$ and $R^2$ can represent are methyl, ethyl, and n-propyl. Preferably $R^1$ and $R^2$ are both methyl, particularly where m is 1.

Thus examples of specific groups which B represents are 3- and 4-dimethylaminomethylphenyl, 5-dimethylaminomethyl-2-thienyl, 5-dimethylaminomethyl-2-furanyl, 5-dimethylaminomethyl-3-pyridyl, 6-dimethylaminomethyl-3-pyridyl and 2-dimethylaminomethyl-4-pyridyl. Preferably B is 5-dimethylaminomethyl-2-furanyl, 6-dimethylaminomethyl-3-pyridyl or 2-dimethylaminomethyl-4-pyridyl.

One group of compounds within the scope of this invention is that where W is phenyl substituted in the 3- or 4-position with $R^1R^2N(CH_2)_m-$. In this group preferably Y is oxygen and X is methylene and preferably the group $R^1R^2N(CH_2)_m-$ is in the 3-position.

A further group of compounds within the scope of this invention is that where W is 2-furanyl or 2-thienyl optionally substituted in the 5-position with $R^1R^2N(CH_2)_m-$; 4-imidazolyl optionally substituted in the 5-position with methyl or bromine; 2-pyridyl or a 3-pyridyl group substituted in position 5 or 6 or a 4-pyridyl group substituted in position 2 or a 2-pyridyl group substituted in position 4 or 5 by a group $R^1R^2N(CH_2)_m$; $R^1$ and $R^2$ are $C_{1-4}$ alkyl or together with the nitrogen atom to which they are attached form a pyrrolidino, piperidino or morpholino group; m is 1 to 4; and pharmaceutically acceptable acid addition salt thereof.

By way of example Z can be hydrogen, methyl, ethyl, n-propyl or n-butyl but preferably Z is hydrogen.

With reference to B examples of $C_{1-4}$ alkyl groups which $R^1$ and $R^2$ can represent are methyl, ethyl, and n-propyl. Preferably $R^1$ and $R^2$ are both methyl, particularly where m is 1.

Thus examples of specific groups which B represents are 3- and 4-dimethylaminomethylphenyl, 5-dimethylaminomethyl-2-thienyl, 5-dimethylaminomethyl-2-furanyl, 5-dimethylaminomethyl-3-pyridyl, 6-dimethylaminomethyl-3-pyridyl and 2-dimethylaminomethyl-4-pyridyl. Preferably B is 5-dimethylaminomethyl-2-furanyl, 6-dimethylaminomethyl-3-pyridyl or 2-dimethylaminomethyl-4-pyridyl.

One group of compounds within the scope of this invention is that where W is phenyl substituted in the 3- or 4-position with $R^1R^2N(CH_2)_m-$. In this group preferably Y is oxygen and X is methylene and preferably the group $R^1R^2N(CH_2)_m-$ is in the 3-position.

A further group of compounds within the scope of this invention is that where W is 2-furanyl or 2-thienyl optionally substituted in the 5-position with $R^1R^2N(CH_2)_m-$; 4-imidazolyl optionally substituted in the 5-position with methyl or bromine; 2-pyridyl 2-[2-(5-Methyl-4-imidazolylmethylthio)ethylamino]-5-(3-dimethylaminomethylbenzyl)-4-pyrimidone,
2-[2-(5-Methyl-4-imidazolylmethylthio)ethylamino]-5-(5-dimethylaminomethyl-2-thienylmethyl)-4-pyrimidone,
2-[2-(5-Dimethylaminomethyl-2-thienylmethylthio)ethylamino]-5-(5-dimethylaminomethyl-2-thienylmethyl)-4-pyrimidone,
2-[2-(2-Guanidino-4-thiazolylmethylthio)ethylamino]-5-(5-dimethylaminomethyl-2-thienylmethyl)-4-pyrimidone,
2-[2-(2-Guanidino-4-thiazolylmethylthio)ethylamino]-5-(4-dimethylaminomethylbenzyl)-4-pyrimidone,
2-[3-(3-Dimethylaminomethylphenoxy)propylamino]-5-(5-dimethylaminomethyl-2-thienylmethyl)-4-pyrimidone,
2-[3-(3-Dimethylaminomethylphenoxy)propylamino]-5-(4-dimethylaminomethylbenzyl)-4-pyrimidone and their pharmaceutically acceptable acid addition salts.

Examples of compounds within the scope of the invention having the preferred group B are:
2-[2-(5-Methyl-4-imidazolylmethylthio)ethylamino]-5-(5-dimethylaminomethyl-2-furanylmethyl)-4-pyrimidone,
2-[2-(2-Guanidino-4-thiazolylmethylthio)ethylamino]-5-(5-dimethylaminomethyl-2-furanylmethyl)-4-pyrimidone,
2-[3-(3-Dimethylaminomethylphenoxy)propylamino]-5-(5-dimethylaminomethyl-2-furanylmethyl)-4-pyrimidone,
2-[2-(5-Methyl-4-imidazolylmethylthio)ethylamino]-5-(6-dimethylaminomethyl-3-pyridylmethyl)-4-pyrimidone and their pharmaceutically acceptable acid addition salts.

Examples of compounds within the scope of the invention having the preferred group W are:
2-[2-(5-Dimethylaminomethyl-2-furanylmethylthio)ethylamino]-5-(5-dimethylaminomethyl-2-thienylmethyl)-4-pyrimidone,
2-[2-(5-Dimethylaminomethyl-2-furanylmethylthio)ethylamino]-5-(3-dimethylaminomethylbenzyl)-4-pyrimidone, and their pharmaceutically acceptable acid addition salts.

Examples of compounds having the preferred groups W, Y, X and B are:
2-[2-(5-Dimethylaminomethyl-2-furanylmethylthio)ethylamino]-5-(5-dimethylaminomethyl-2-furanylmethyl)-4-pyrimidone,
2-[2-(5-Dimethylaminomethyl-2-furanylmethylthio)ethylamino]-5-(2-dimethylaminomethyl-4-pyridylmethyl)-4-pyrimidone,
2-[2-(5-Dimethylaminomethyl-2-furanylmethylthio)ethylamino]-5-(6-dimethylaminomethyl-3-pyridylmethyl)-4-pyrimidone and their pharmaceutically acceptable acid addition salts.

Compounds of formula (I) are bases and can form pharmaceutically acceptable salts with acids, for example those with hydrochloric, hydrobromic, sulphuric, phosphoric, acetic, citric and maleic acids.

According to this invention compounds of formula (I) and their salts can be prepared by reacting a compound of formula (II):

WYD   (II)

where W and Y are as defined with reference to formula (I) and D is —XCH$_2$CH$_2$NH$_2$ or, provided that Y is methylene, a group displacable with thiol with a pyrimidone derivative of formula (III):

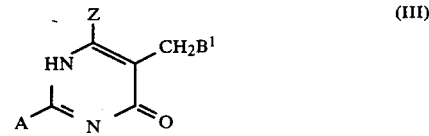

where B$^1$ is 2-furanyl, 2-thienyl or B, where B and Z are as defined with reference to formula (I), and A is a group displaceable by an amine when D is —XCH$_2$CH$_2$NH$_2$ or A is HS—CH$_2$—CH$_2$NH when D is a group displaceable with thiol, and thereafter when B$^1$ is 2-furanyl or 2-thienyl, and optionally when W is 2-furanyl or 2-thienyl reacting the product so obtained with a Mannich reagent supplying the substituent R$^1$R$^2$N(CH$_2$)$_m$— where m is 1, and thereafter converting a compound of formula (I) so obtained into a salt.

Examples of groups displaceable by thiol are hydroxy, alkanoyloxy (preferably acetoxy), methanesulphonyloxy, p-toluenesulphonyloxy, trifluoromethanesulphonyloxy, C$_{1-4}$ alkoxy (preferably methoxy), chlorine, bromine and triarylphosphonium (preferably triphenylphosphonium).

When W contains the group R$^1$R$^2$N(CH$_2$)Hd m— preferably D is hydroxy, C$_{1-4}$ alkoxy or acetoxy and the reaction is carried out under acidic conditions, for example in acetic acid or in aqueous hydrochloric or hydrobromic acid. When W is 2-furanyl or 2-thienyl preferably D is sulphonyloxy, chlorine, bromine or triarylphosphonium and the reaction is carried out in the presence of a base, for example in the presence of sodium ethoxide in ethanol. Preferably D is hydroxy or chlorine.

Examples of leaving groups displaceable by amines are where A is nitroamino, C$_{1-4}$ alkylthio, chlorine or bromine. Preferably the group A is nitroamino.

The process where A is a leaving group displaceable by amines can be carried out at elevated temperature e.g. 150° C., or at reflux in the presence of a high boiling solvent e.g. in pyridine. When A is nitroamino the reaction can be carried out in an alkanol for example ethanol at reflux.

Mannich reagents can be prepared in situ from an amine R$^1$R$^2$NH where R$^1$ and R$^2$ are as defined with reference to formula (I) and formaldehyde, or where R$^1$ and R$^2$ are both C$_{1-4}$ alkyl, can be preformed e.g. from a di(C$_{1-4}$ alkyl)methylene ammonium salt particularly dimethylmethylene ammonium chloride or iodide or a bis-(di C$_{1-4}$ alkylamino)methane, in particular bis(-dimethylamino)methane.

This process involving a Mannich reagent is an example of the Mannich Reaction and can be carried out under conditions generally used for this type of reaction.

Acid addition salts of compounds of formula (I) can conveniently be formed from the corresponding bases by standard procedures for example by reacting the base with an acid in a C$_{1-4}$ alkanol or by the use of ion exchange resins to form the required salt. Salts of compounds of formula (I) can also be interconverted using an ion exchange resin.

Compounds of formula (II) are known or can be made by analogy with known methods. In particular, compounds of formula (II) where D is —XCH₂CH₂NH₂ [amines of formula (II)] are well documented for example those in which W is a 2-thiazolyl group, a 4-imidazolyl group optionally substituted in the 5-position with methyl or bromine or a 2-pyridyl group optionally substituted in the 3-position with $C_{1-4}$ alkyl, $C_{1-4}$ alkoxy, halogen, amino or hydroxy, and Y is CH₂ and X is CH₂ or sulphur are disclosed in U.S. Pat. Nos. 3,734,924, 3,736,331, 3,868,457, 4,083,983, 3,905,984, 3,950,353 and 4,159,329. Amines of formula (II) where W is 2-furanyl and 2-thienyl substituted in the 5-position with a group $R^1R^2N(CH_2)_m$— and Y is CH₂ and X is CH₂ or sulphur, are disclosed in U.S. Pat. Nos. 4,128,658 and 4,239,769. Amines of formula (II) where W is a phenyl group substituted in position 3- or 4- with a group $R^1R^2N(CH_2)_m$— and Y is oxygen or methylene and X is methylene or sulphur are disclosed in Belgian Patent Specification No. 867106 and European patent application No. 80300478.7.

Amines of formula (II) where W is 2-guanidino-4-thiazolyl, Y is methylene and X is methylene or sulphur are disclosed in U.S. Pat. Nos. 4,165,377 and 4,165,378.

Pyrimidone derivatives of formula (III) where B¹ is 2-furanyl or 2-thienyl can be made by known methods as disclosed in for example European Pat. No. 0 004 793 and U.S. Pat. Nos. 4,159,329 and 4,216,318.

Pyrimidones of formula (III) where B¹ is B and A is nitroamino can be prepared by reacting nitroguanidine with a β-oxoester of formula (IV):

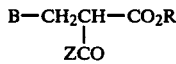

where B and Z are as defined with reference to formula (III) and R is $C_{1-4}$ alkyl, in the presence of base.

Examples of suitable bases include alkali metal hydroxides and $C_{1-4}$ alkoxides, sodium hydride, and quaternary ammonium hydroxides, for example benzyltrimethylammonium hydroxide. Preferably the base is sodium ethoxide or sodium methoxide. The reaction can be carried out in the presence of a solvent the choice of which is not critical to the success of the process provided that it is substantially inert to the reagents and product. Preferably the solvent is a $C_{1-4}$ alkanol, (for example, methanol, ethanol or propanol) or dimethylformamide.

Pyrimidone derivatives of formula (III) where B¹ is B and A is $C_{1-4}$ alkylthio can be prepared by reacting a β-oxoester of formula (IV) above with thiourea to form a 2-thiouracil of formula (V):

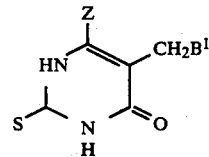

where Z and B are as defined with reference to formula (III), which can be then alkylated with a $C_{1-4}$ alkyl halide or sulphate.

Pyrimidones of formula (III) where B¹ is B and A is chlorine or bromine can be prepared by reacting a β-oxoester of formula (IV) with guanidine to form an amino pyrimidone (VI):

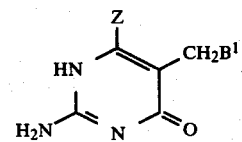

where Z and B are as defined with reference to formula (III) and converting the amino group into chlorine or bromine by reacting the aminopyrimidone (VI) with sodium nitrite, the corresponding hydrohalic acid and corresponding cuprous halide.

Pyrimidones of formula (III) where A is HSCH₂CH₂NH— can be prepared by reacting an amine of formula (VII):

$$GS—CH_2CH_2NH_2 \quad (VII)$$

where G is hydrogen or a thiol-protecting group (for example trityl, 4-methoxybenzyl or the residue of the disulphide viz NH₂CH₂CH₂S—) with a pyrimidone of formula (III) where A is a group which is displaceable with amine as previously discussed and thereafter removing the thiol protecting group.

Pyrimidone derivatives of formula (III) where B¹ is B that is to say compounds of formula (IIIa):

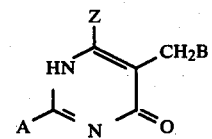

where A is a group displacable by an amine or is HSCH₂CH₂NH— and Z and B are as defined with reference to formula (I) are novel and form a further aspect of this invention.

Amines of formula (VII) are known or can be prepared by analogy with known methods.

Compounds of formula (II) where D is —OH are known or can be made by analogy with known methods.

The activity of the compounds of formula (I) as histamine H₂-antagonists can be demonstrated by the inhibition of histamine-stimulated secretion of gastric acid from the lumen-perfused stomachs of rats anaesthetised with urethane. This procedure is referred to in Ash and Schild, Brit. J. Pharmac. Chemother., 27, 247 (1966). The compounds of Examples 1 to 14 hereafter caused 50% inhibition of maximal acid secretion at doses of less than 0.5 micromole kg⁻¹ i.v. Their activity as histamine H₂-antagonists can also be demonstrated by their ability to inhibit other actions of histamine which, according to the above mentioned paper of Ash and Schild, are not mediated by histamine H₂-receptors. For example, they inhibit the actions of histamine on the isolated guinea pig atrium. The potency of these compounds is illustrated by the effective dose producing 50% inhibition of the histamine-induced tachycardia in the isolated guinea pig atrium (less than 10⁻⁶ Molar).

In order to use a compound of formula (I) or a pharmaceutically acceptable salt thereof for medical purposes, it is normally formulated in accordance with standard pharmaceutical practice as a pharmaceutical composition.

The invention further provides pharmaceutical compositions comprising a compound of formula (I) above or a pharmaceutically acceptable acid addition salt thereof together with a pharmaceutically acceptable carrier.

Compounds of formula (I) and their pharmaceutically acceptable acid addition salts may be administered orally, parenterally, cutaneously or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the compositions is in the form of a tablet, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil.

Typical compositions for administration to the skin include lotions and creams in which the compound of formula (I) or a salt thereof is dispersed in a liquid vehicle.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

Preferably the composition is in unit dose form for example a tablet or capsule so that the patient may administer to himself a single dose.

Each dosage unit contains preferably from 15 to 250 mg of a compound of formula (I) or a pharmaceutically acceptable acid addition salt thereof calculated as the free base.

This invention also provides a method of blocking histamine $H_2$-receptors which comprises administering to an animal an effective amount to block said receptors of a compound of formula (I) or a pharmaceutically acceptable acid addition salt thereof.

The pharmaceutical compositions of the invention will normally be administered to man for the treatment of gastric and duodenal ulcers and other conditions caused or exacerbated by gastric acidity in the same general manner as that employed for known histamine $H_2$-antagonist, due allowance being made in terms of dose levels for the potency of the compound of the present invention relative to known histamine $H_2$-antagonist drugs. The daily dosage regimen for an adult patient is an oral dose between 15 mg and 1500 mg and preferably between 20 mg and 250 mg or an intravenous, subcutaneous or intra-muscular dose of between 1.5 mg and 150 mg and preferably between 5 mg and 20 mg of compound of formula (I) or pharmaceutically acceptable salt thereof calculated as the free base, the composition being administered 1 to 6 times per day.

The following Examples illustrate the invention.

EXAMPLES

EXAMPLE 1

(i) 5-(Dimethylaminomethyl)thiophene-2-carboxaldehyde (40.09 g) and piperidine (3 ml) were added to a solution of malonic acid (24.65 g) in pyridine (150 ml). The mixture was stirred under reflux for 7 hours. During the reaction a solid precipitated and slowly re-dissolved. The solution was allowed to cool and was then poured on to 2 M hydrochloric acid (150 ml). The volume of the solution was reduced to about 120 ml by evaporation at reduced pressure and extracted with diethyl ether. The ether extracts were washed with water. The aqueous phase was cooled and the solid, which precipitated out, was filtered off and washed with water-isopropanol. More solid was obtained by evaporating the filtrate to about 100 ml and adding isopropanol and cooling the mixture in ice for about 15 minutes. This solid was filtered off, and washed with isopropanol. The solids were combined and recrystallised from isopropanol-water to give 3-(5-dimethylaminomethyl-2-thienyl)acrylic acid (27.45 g) m.p. 223.5°–225° C.

(ii) 3-(5-Dimethylaminomethyl-2-thienyl)acrylic acid (33.31 g) was dissolved in ethanol (150 ml) and acidified with conc. sulphuric acid (10 ml). The solution was refluxed for 18 hours, allowed to cool then was poured on to a mixture of ice and aqueous ammonia (0.88% w/w 30 ml). The ice was allowed to melt, then the aqueous solution extracted with ether and the combined ether-extracts washed with water and dried over $MgSO_4$. Ether was evaporated at reduced pressure to give ethyl 3-(5-dimethylaminomethyl-2-thienyl) acrylate (30.30 g) as a straw-coloured oil.

(iii) A solution of ethyl 3-(5-dimethylaminomethyl-2-thienyl)acrylate (30.30 g) in ethanol (175 ml) was hydrogenated (initial press. 344 kPa) over a total of 8.5 hr at a temperature of between 55°–60° C. in the presence of 10% palladium on charcoal catalyst (ca. 10 g) used in two portions. The first portion was added to the reaction mixture initially and the second after 5.5 hrs. The catalyst was filtered off over diatomecous earth and washed with ethanol. The filtrate was evaporated at reduced pressure to give ethyl 3-(5-dimethylaminomethyl-2-thienyl)-propionate (29.91 g) as a colourless oil.

(iv) A mixture of ethyl 3-(5-dimethylaminomethyl-2-thienyl) propionate (29.91 g) and ethyl formate (13.77 g; 15 ml) was added dropwise with stirring to a suspension of sodium hydride in oil (57% in oil; 6.52 g) in 1,2-dimethoxyethane (45 ml) which had been precooled to −5° C. The temperature was kept at from −5° to −2° C. throughout the addition. The mixture was then allowed to warm gradually to room temperature and to stand for about 16 hrs. The mixture was poured on to ice which melted to give a brown solution which was evaporated to dryness giving an oil. The oil was mixed with hot acetone and the mixture was filtered through diatomecous earth and the acetone evaporated yielding ethyl-3-(5-dimethylaminomethyl-2-thienyl)2-formyl-propionate (32.92 g) as an oil.

(v) Nitroguanidine (16.92 g containing 25% water) and methanol (35 ml) were added to a solution of sodium (4.21 g) in methanol (95 ml), and the mixture was heated under reflux with stirring for 45 minutes. A solution of ethyl 3-(5-dimethylaminomethyl-2-thienyl)-2-formyl-propionate (32.85 g) in methanol (90 ml) was then added to this refluxing mixture with stirring over 1.25 hr. The mixture so obtained was heated under reflux with stirring for a further 22 hr. The methanol was evaporated at reduced pressure and the residue dissolved in water. The solution so obtained was extracted with chloroform and the combined extracts were washed with water. The aqueous phase and water washings were combined and the water evaporated at reduced pressure. The residue was dried by azeotroping with isopropanol. The residue was mixed with a small amount of water, warmed and allowed to cool, and the insoluble residue was filtered, washed with water and ethanol and dried yielding 2-nitro-amino-5-(5-dimethylamino-2-thienylmethyl)-4-pyrimidone (6.53 g) m.p. 228°–232° C. (decomp).

(vi) A mixture of 2-(5-methyl-4-imidazolylmethylthio)ethylamine (1.37 g) and 2-nitroamino-5-(5-dimethylaminomethyl-2-thienylmethyl)-4-pyrimidone (2.32 g) in ethanol was heated under reflux for 48 hrs. The ethanol was evaporated at reduced pressure yielding 2-[2-(5-methyl-4-imidazolyl-methylthio)ethylamino]-5-(5-dimethylaminomethyl-2-thienylmethyl)-4-pyrimidone as a glassy residue which was washed with hot water by decantation. The residue was dissolved in isopropanol and a solution of ethanolic hydrochloric acid (3 ml) was added. Excess of solvent was removed at reduced pressure and trihydrochloride crystallized as a light buff solid (3.11 g). The solid was recrystallized from methanol-ethanol (2.36 g) 185.5°–188.5° C.

EXAMPLE 2

A mixture of 2-(5-dimethylaminomethyl-2-furanylmethylthio)ethylamine (1.64 g) and 2-nitroamino-5-(5-dimethylaminomethyl-2-thienylmethyl)-4-pyrimidone (2.01 g) in ethanol (10 ml) was heated under reflux for 30 hr. The ethanol was evaporated in vacuo to yield 2-[2-(5-dimethylaminomethyl-2-furanylmethylthio)ethylamino]-5-(5-dimethylaminomethyl-2-thienylmethyl)-4-pyrimidone as a brown oil which was washed with hot water by decantation. The residue was dissolved in isopropanol and an excess of ethanolic hydrochloric acid was added to the solution.

Excess of solvent was evaporated in vacuo and the residue was recrystallized from isopropanol-methanol containing ethanolic HCl and then from ethanol-methanol to give the trihydrochloride (2.72 g) m.p. 197°–200° C.

EXAMPLE 3

[2-(2-Guanidino-4-thiazolylmethylthio)]ethylamino dihydrochloride (2.43 g) was dissolved in ethanolic sodium ethoxide solution (0.37 g sodium; 15 ml ethanol). The solution was stirred for 1 hr and the sodium cholride deposited during this time was removed by filtration. 2-Nitroamino-5-(5-dimethylaminomethyl-2-thienylmethyl)-4-pyrimidone (2.00 g) was added to the solution and the mixture as heated under reflux for 48 hr. The ethanol was evaporated at reduced pressure and the residue was precipitated twice from solution in the minimum quantity of ethanol by dropwise addition of water. 2-[2-(2-Guanidino-4-thiazolylmethylthio)ethylamino]-5-(5-dimethylaminomethyl-2-thienylmethyl)-4-pyrimidone was recovered as an oily solid.

The oily solid was dissolved in ethanol and decolourised with carbon. The solvent was evaporated under reduced pressure from the decolourised solution giving a yellow oil which solidified on trituration giving a white solid which was recrystallised from diethyl ether/isopropanol and then from ethanolic hydrochloric acid/isopropanol to give the trihydrochloride (0.59 g) m.p. 164°–6° C.

EXAMPLE 4

(i) A mixture of 4-dimethylaminomethylbenzaldehyde (32.64 g), monoethylmalonate (29.07 g), pyridine (100 ml) and piperidine (2 ml) were heated under reflux with stirring for 5 hr. The pyridine was evaporated at reduced pressure, and the oily residue was extracted with diethyl ether. The combined ether extracts were washed with water and dried over magnesium sulphate. The ether was evaporated at reduced pressure to yield ethyl 4-(dimethylaminomethyl)cinnamate as a light straw coloured oil (46.57 g).

(ii) A solution of ethyl 4-(dimethylaminomethyl)cinnamate in ethanol (170 ml) was hydrogenated using palladium on charcoal (0.5 g) at a temperature of 36°–37° C. and hydrogen at an initial pressure of 344 kPa until the theoretical uptake of hydrogen was recorded.

The solution was filtered over diatomecous earth to remove catalyst and the filter medium was washed with ethanol. The combined filtrate and washings were evaporated to yield ethyl 3-(4-dimethylaminomethylphenyl)propionate (45.97 g) as a light straw-coloured oil.

(iii) A mixture of ethyl 3-(4-dimethylaminomethylphenyl)propionate (45.97 g) and ethyl formate (21.70 g) was added dropwise with stirring to a suspension of sodium hydride (50% in oil; 11.72 g) in dimethoxyethane (70 ml) which had been precooled to a temperature between −5° and −10° C. The temperature was maintain below −5° C. throughout the addition. When the addition was complete, the mixture was allowed gradually to warm to room temperature while being stirred and then to stand for about 16 hr.

The mixture was poured on to ice which melted giving a brown aqueous solution which was acidified to pH 6 with glacial acetic acid and the aquious phase evaporated. The organic component of the residue was extracted with hot acetone and isopropanol leaving an insoluble inorganic residue which was filtered off and washed with additional hot acetone and isopropanol. The filtrate and washings were evaporated to dryness, and the residue dissolved in water and the solution neutralised to pH 7 with sodium bicarbonate. The aqueous solution was extracted with ethyl acetate, and the combined organic extracts were washed with water, dried with magnesium sulphate and evaporated at reduced pressure yielding ethyl 3-(4-dimethylaminomethylphenyl)-2-formylpropionate (15.27 g) as light-buff solid m.p. 95.5°–97° C.

(iv) Nitroguanidine (7.92 g containing 25% w/w water) was washed with methanol (10 ml) into sodium methoxide (from 1.97 g sodium) in methanol (85 ml). The mixture was stirred while heating under reflux for 45 min and ethyl 3-(4-dimethylaminomethylbenzyl)-2-formylpropionate (15.03 g) was added portionwise over 1.25 hr and washed in with methanol (15 ml). The mixture was stirred while being heated under reflux for a further 22 hr.

The methanol was evaporated at reduced pressure and the residue dissolved in water (100 ml) and extracted with chloroform. The combined chloroform extracts were washed with water. Ther aqueous layer and water washings were acidified to pH 5 with glacial acetic acid. The water was evaporated at reduced pressure and isoporpanol (80 ml) was added. The solid which gradually precipitated was filtered washed with water and isopropanol, and dried in vacuo yielding 2-nitroamino-5-(4-dimethylaminomethylbenzyl)-4-pyrimidone (9.90 g) as a white solid m.p. 214°–7° C.

(v) A mixture of 2-(5-methyl-4-imidazolylmethylthio)ethylamine (1.37 g) and 2-nitroamino-5-(4-dimethylaminomethylbenzyl)-4-pyrimidone (2.27 g) in ethanol (12 ml) was heated under reflux for 24 hr. The ethanol was evaporated at reduced pressure giving 2-[2-(5-methyl-4-imidazolylmethylthio)ethylamino]-5-(4-dimethylaminomethylbenzyl)-4-pyrimidone which was washed by mixing it with water, warming the mixture, allowing it to cool over about 16 hr. and decanting the water. The residue was reacted with ethanolic hydrochloric acid (7 ml) and ethanol removed at reduced pressure. The residue was recrystallised from methanol/ethanol to give the trihydrochloride (2.14 g) as a white solid m.p. 213.5°–216° C.

EXAMPLE 5

A mixture of 2-(5-dimethylaminomethyl-2-furanylmethylthio)ethylamine (1.71 g) and 2-nitroamino-5-(4-dimethylamino methylbenzyl)-4-pyrimidone (1.97 g) in ethanol (12 ml) was heated under reflux for 42 hr. The ethanol was evaporated at reduced pressure yielding 2-[2-(5-dimethylaminomethyl-2-furanylmethylthio)ethylamino]-5-(4-dimethylaminomethylbenzyl) 4-pyrimidone as a brown oily residue which was washed with hot water, cooled and mixed with dilute ethanolic hydrochloride acid. Excess of ethanol was evaporated under reduced pressure and the residue was recrystallised from isopropanol/methanol and from ethanol to give the trihydrochloride (1.85 g) as an off-white solid m.p. 180°–184° C.

EXAMPLE 6

(i) A mixture of acetic acid (200 ml), ethyl 3-(2-furanyl) propionate, (32.2 g) dimethyl ammonium chloride (17.92 g) and 30% w/v aqueous formaldehyde (17.04 g) was made and warmed gently until a solution formed. The mixture was allowed to cool and to stand for about 36 hr at room temperature. Acetic acid was removed by evaporation at reduced pressure yielding an oil which was dissolved in water adjusted to basic pH 10-11. The aqueous solution was extracted with ethyl acetate. The ethyl acetate extracts were combined, dried over magnesium sulphate, and ethyl acetate evaporated at reduced pressure to give a brown oil which was distilled to give ethyl 3-(5-dimethylaminomethyl)2-furanyl)propionate as a colourless oil (19.25 g) b.p. 0.7 mm 108°–112° C.

(ii) Ethyl 3-(5-dimethylaminomethyl-2-furanyl)-propionate (19 g) and ethyl formate (9.33 g) were added dropwise with stirring to a suspension of sodium hydride (50% in oil, 4.0 g) in 1,2-dimethoxyethane (50 ml) which had been precooled to −40° C. The temperature was kept below −30° C. throughout the addition and when this was complete the mixture was allowed to warm gradually to room temperature over about 16 hr. A solid brown mass formed which was added to ice. When the ice melted an aqueous solution formed which was extracted with ethyl acetate. The aqueous phase was acidified with acetic acid to pH 4.5 evaporated to dryness at reduced pressure and azeotroped with n-propanol yielding a brown oil. The oil was extracted with hot acetone to remove acetone-insoluble inorganic material which were filtered from the acetone solution and washed with hot acetone. The acetone solution was evaporated to dryness yielding ethyl 3-(5-dimethylaminomethyl-2-furanyl)-2-formyl propionate (21.22 g) which was used in the next step without purification.

(iii) Nitroguanidine (10.85 g containing 25% w/w water) was added to a solution of sodium (5.75 g) in methanol (100 ml) and the mixture was stirred while being heated under reflux for 0.5 hr. The mixture was allowed to cool and a solution of ethyl 3-(5-dimethylaminomethyl-2-furanyl)-2-formylpropionate (21.22 g) in methanol (80 ml) was added dropwise to the cool mixture. The mixture so obtained was then stirred while being heated under reflux for 18 hr after which time the solvent was evaporated under reduced pressure and the residue was mixed with hot acetone, producing a solution and a solid residue which was removed by filtration washed with more hot acetone and the acetone washings were combined with the solution. The combined solution was evaporated at reduced pressure to give an oil which was crystallised from isopropanol to give 2-nitroamino-5-(5-dimethylaminomethyl-2-furanylmethyl-4-pyrimidone (5.42 g) m.p. 210° C. (decomp).

(iv) A solution of 2-(5-methyl-4-imidazolylmethylthio)ethylamine (1.28 g) and 2-nitroamino-5-(5-dimethylaminomethyl-2-furanylmethyl)-4-pyrimidone (2.2 g) in pyridine (20 ml) was heated under reflux for about 16 hr. The pyridine was evaporated at reduced pressure, azeotroped with water to remove pyridine and water was removed by azeotroping with n-propanol. The oily residue was chromatographed on a silica column eluting with methanol in ethyl acetate. Evaporation of the eluant yielded a glassy solid residue which was dissolved in methanol. Ether was added to precipitate 2-[2-(5-methyl-4-imidazolylmethylthio)ethylamino]-5-(5-dimethylaminomethyl-2-furanylmethyl)-4-pyrimidone (1.19 g) as a white solid m.p. 108°–110° C.

EXAMPLE 7

A solution of 2-(5-dimethylaminomethyl-2-furanylmethylthio)ethylamine (1.29 g) and 2-nitroamino-5-(5-dimethylaminomethyl-2-furanylmethyl)-4-pyrimidone in pyridine (15 ml) was heated under reflux for about 20 hr. The pyridine was evaporated at reduced pressure. The last traces of pyridine were removed by azeotroping with water and water removed by azeotroping with n-propanol. The oily residue was chromatographed on a silica gel column eluting with methanol in ethyl acetate (10% v/v). Evaporation of the eluant yielded 2-[2-(5-dimethylaminomethyl-2-furanylmethylthio)ethylamino]-5-(5-dimethylaminomethyl-2-furanylmethyl)-4-pyrimidone as an oil which was converted to its trihydrochloride using an excess of ethanolic HCl. The salt was recrystallised from isopropanol yielding a white solid (0.72 g) m.p. 181°–183° C.

EXAMPLE 8

2-(2-Guanidino-4-thiazolylmethylthio)ethylamine dihydrochloride (2.00 g) was added to a solution of sodium (0.3 g) in ethanol (15 ml). After refluxing the solution for 0.5 hour the ethanol was evaporated at reduced pressure and dry pyridine (40 ml) added. 2-Nitroamino-5-(5-dimethylamino-methyl-2-furanyl)-4-pyrimidone (1.90 g) was added and the mixture refluxed for 20 hr. Pyridine was evaporated at reduced pressure and the oily residue azeotroped with water. The residue was further washed with water and the water decanted. The residual oil was then azeotroped with n-propanol and treated with de-colourising charcoal. The de-colourised residue was dissolved in ethanolic HCl and evaporated to dryness at reduced pressure. The hydrochloride salt produced which was very hygroscopic, was converted into the free base by dissolving it in water, basifying the aqueous solution with sodium bi-carbonate and extracting with ethyl acetate. The ethyl acetate was dried and evaporated to dryness to give a yellow solid which was re-crystallised from ethyl acetate to give 2-[2-(guanidino-4-thiazolylmethylthio)ethylamino]-5-(5-dimethylaminomethyl-2-furanylmethyl)-4-pyrimidone (0.34 g), m.p. 113°–116° C.

EXAMPLE 9

A solution of 2-(5-dimethylaminomethyl-2-thienylmethylthio)ethylamine (1.47 g) and 2-nitroamino-5-(5-dimethylaminomethyl-2-thienylmethyl)-4-pyrimidone (2.0 g) in pyridine (10 ml) was refluxed overnight. The pyridine was removed under reduced pressure and the last traces of pyridine were removed by azeotroping with water yielding 2-(5-dimethylaminomethyl-2-thienylmethylthio)ethylamino-5-(5-dimethylaminomethyl-2-thienylmethyl)-4-pyrimidone as an oil. The resultant oil was washed by decantation with water.

The brown oil so produced was dissolved in diethyl ether and ethanolic hydrochloric acid solution was added. The liquid was evaporated and the residual solid was recrystallised from methanol/ethanol to yield the hydrochloride (1.9 g) m.p. 212°–215° C.

EXAMPLE 10

(i) A mixture of ethyl 3-(6-methyl-3-pyridyl) propionate (38.65 g), hydrogen peroxide (30%, 25 ml) and glacial acetic acid (100 ml) were stirred at 95°–100° C. for 5.5 hr. The acetic acid was evaporated at reduced pressure and the residue diluted to with water (to about 100 ml.) The aqueous mixture was taken to pH 9 with aqueous sodium carbonate solution and extracted with ethyl acetate. The extracts were washed with water, dried (Mg SO$_4$) and the ethyl acetate evaporated at reduced pressure to yield ethyl 3-(6-methyl-3-pyridyl)-propionate N-oxide as a brown oil (31.51 g). Reduction of the aqueous layer to (ca 100 ml) and continuous extraction for 6 hr with ethyl acetate yielded a further amount (3.38 g) of the product also as a brown oil.

(ii) Trifluoroacetic anhydride (100.59 g) was added dropwise over 45 min with stirring to a pre-cooled (2° C.) solution of ethyl 3-(6-methyl-3-pyridyl)-propionate N-oxide (59.40 g), 0.284 mol) in dry dichloromethane (500 ml) maintaining the temperature between 5°–8° C. The mixture was then allowed to stand for 20 hr at room temperature with light excluded. Methanol (40 ml) was added to the solution and the dichloromethane removed by distillation. The residue was dissolved in water and taken to pH 6 with aqueous sodium bicarbonate solution. The solution was extracted with chloroform, the chloroform extracts washed with water, dried (MgSO$_4$) and the chloroform removed by distillation to yield a brown oil which was dissolved in methanol (120 ml) and reacted with ethanolic hydrochloric acid (50 ml). Evaporation of the solvent yielded ethyl 4-(6-hydroxymethyl-3-pyridyl)propionate hydrochloride as a brown oil (66.57 g).

(iii) Thionyl chloride (35.5 ml) was added dropwise with stirring over 15 min to a pre-cooled solution (0° C.) of ethyl 3-(6-hydroxymethyl-3-pyridyl)propionate hydrochloride (66.57 g) in chloroform (300 ml) maintaining the temperature at 0°–2° C. When addition was complete the reaction mixture was stirred for a further 2.5 hr, allowed to warm to room temperature and then warmed to 40° C. for ca 15 min. Chloroform and the excess of thionyl chloride were evaporated at reduced pressure. The residual thionyl chloride was removed by adding benzene and evaporating at reduced pressure to yielding a brown oil.

The brown oil was dissolved in ethanol (300 ml) the solution cooled (0° C.) and a solution of dimethylamine (33% w/v) in ethanol was added dropwise with stirring over 20 min. When the addition was complete stirring was continued for 1 hr while the reaction mixture warmed to room temperature. The reaction mixture was then allowed to stand overnight.

The ethanol was evaporated at reduced pressure, the residue dissolved in water and brought to pH 9 with aqueous sodium bicarbonate solution. The aqueous solution was extracted with ethyl acetate washed with water, dried (MgSO$_4$) and evaporated at reduced pressure to yield ethyl 4-(6-dimethylaminomethyl-3-pyridyl)propionate (55.01 g) as a brown oil. The oil was dissolved in methanol and reacted with an excess of ethanolic hydrochloric acid. Evaporation of the solvent at reduced pressure yielded an oil which was recrystallised from isopropanol/ethyl acetate to give 3-(6-dimethylaminomethyl-3-pyridyl)-propionate dihydrochloride (46.85 g) as a light buff solid m.p. 124°–8° C. Evaporation of the mother liquor produced a residue which was recrystallised from isopropanol/ethyl acetate to produce a further amount (1.55 g) of the product.

(iv) A mixture of vacuum dried ethyl 3-(6-dimethylaminomethyl-3-pyridyl)-propionate (28.02 g) by neutralization of the dihydrochloride salt with sodium bicarbonate, and ethyl formate (13.18 g) was added dropwise with stirring to a cooled (−2° C.) suspension of sodium hydride (50% in oil, 7.12 g) in 1,2-dimethoxyethane (50 ml) over 30 min keeping the temperature of the reaction mixture at 0° C. Stirring was continued while the reaction mixture was allowed to warm to room temperature and the mixture was then allowed to stand overnight.

The reaction mixture was poured on to ice and a brown solution formed which was extracted with petroleum ether (b.p. 40°–60° C.) and diethyl ether. The extracts combined and washed with water. The water washings were combined with the aqueous solution and the water was evaporated and last traces removed by azetroping with n-propanol to yield 2-formyl-3-(6-dimethylaminomethyl-3-pyridyl)-propionate (22.81 g) as a brown oil.

(v) Nitroguanidine (11.96 g containing 25% w/w water) was washed with methanol (15 ml) into a solution of sodium methoxide in methanol (from 2.97 g sodium and 55 ml methanol). The mixture was stirred for 45 min under reflux and then a solution of ethyl 2-formyl-3-(6-dimethylaminomethyl-3-pyridyl)propionate (22.78 g) in methanol (50 ml) was added dropwise over 1.25 hr and the mixture was then refluxed for 19 hr.

The methanol was evaporated at reduced pressure and the residue dissolved in water (100 ml). The aqueous solution was extracted with chloroform, and the chloroform extracts washed with water. The aqueous phase was combined with the water washing and brought to pH 5 with acetic acid. The solvent was evaporated at reduced pressure and dried by azetroping with isopropanol. The residue was extracted twice with boiling acetone/n-propanol and recrystallised from water to yield 2-nitroamino-5-(6-dimethylaminomethyl-3-pyridylmethyl)-4-pyrimidone (9.31 g) as a pale green solid m.p. 234°–8° C.

(vi) A mixture of 2-(5-methyl-4-imidazolylmethylthio)ethylamine (1.37 g), 2-nitroamino-5-(6-dimethylaminomethyl-3-pyridylmethyl)-4-pyrimidone (2.28 g) in pyridine were heated under reflux for 22 hr. The pyridine (12 ml) was evaporated at reduced pressure yielding [2-(5-methyl-4-imidazolyl-methylthio)ethylamino]-5-(6-dimethylaminomethyl-3-pyridylmethyl)-4-pyrimidone as a brown oily residue washed with water by decantation. The residue was dissolved in dilute ethanolic hydrochloric acid and the excess of solvent evaporated at reduced pressure. The residue was recrystallised from methanol/dilute ethanolic hydrochloric acid and then twice from methanol/ethanol to yield the tetrahydrochloride (0.82 g) as a light buff solid m.p. 167°–170° C.

EXAMPLE 11

A mixture of 2-(5-dimethylaminomethyl-2-furanylmethylthio)ethylamine (1.71 g) and 2-nitroamino-5-(6-dimethylaminomethyl-3-pyridylmethyl)-4-pyrimidone (1.98 g) in pyridine (12 ml) was refluxed for 22 hr, allowed to cool and the pyridine evaporated at reduced pressure. The residue was washed by decantation with hot water, dissolved in dilute ethanolic hydrochloric acid, and the solvent evaporated yielding 2-[2-(5-dimethylaminomethyl-2-furanylmethylthio)ethylamino]-5-(6-dimethylaminomethyl-3-pyridylmethyl)-4-pyrimidone. The residue was recrystallised from methanol/dilute ethanolic hydrochloric acid and from methanol/ethanol to give the 3.8 hydrochloride 1.4 hydrate (0.85 g) as a light buff solid m.p. 142°–5° C. Evaporation of the mother liquors and recrystallisation of the residue from methanol/ethanol yields more product (0.62 g) m.p. 138°–142° C.

EXAMPLE 12

(i) Raney nickel (ca 7 g) was added to a solution of 3-dimethylaminomethylbenzonitrile (78.30 g) and sodium hypophosphite monohydrate (170.0 g) in water acetic acid pyridine 1:1:2 (1600 ml). The mixture was stirred for 3 hr at 43°–45° C. and then allow to cool.

The Raney nickel was removed by filtration through diatomaceous earth and the filter bed was washed with ethanol. The combined washings and filtrate were evaporated at reduced pressure to a smaller volume (ca 600 ml) and diluted with water (250 ml). The volume of the solution was again reduced (to ca 600 ml) taken to pH 8 with aqueous potassium carbonate solution and extracted with ethyl acetate. The extract was washed with water, dried (MgSO$_4$) and the solvent evaporated to yield 3-dimethylaminomethylbenzaldehyde (62.88 g) as a straw coloured liquid.

(ii) A mixture of 3-dimethylaminomethylbenzaldehyde (32.64 g) monomethylmalonate (29.07 g) pyridine (100 ml) and piperidine (2 ml) were heated under reflux with stirring for 5 hr. The reaction mixture was allowed to cool and the pyridine removed at reduced pressure. The residue was dissolved in diethyl ether, the etherial solution washed with water, dried (MgSO$_4$) and evaporated at reduced pressure and dried in vacuo to yield ethyl 3-(dimethylaminomethyl)cinnamate (40.39 g) as a straw coloured oil.

(iii) A mixture of ethyl 3-(dimethylaminomethyl)cinnamate (40.39 g), Palladium on charcoal (10% ca 0.3 g) in ethanol (170 ml) were hydrogenated at an initial pressure of 344 kPa until a theoretical uptake of hydrogen was recorded. The catalyst was removed by filtration over a diatomaceous earth washed with ethanol and the combined filtrate and washings were evaporated at reduced pressure to give ethyl 3-(3-dimethylamino-methylphenyl)propionate (38.63 g) as a pale straw-coloured liquid.

(iv) A mixture of ethyl 3-(3-dimethylaminomethylphenyl)propionate (38.63 g) and ethyl formate (18.25 g) was added dropwise with stirring to a pre-cooled (−5° C.) suspension of sodium hydride (50% in oil, 9.85 g) in 1,2-dimethoxyethane (60 ml) over 1.75 hr keeping the temperature of the reaction mixture below 0° C. throughout the addition. The mixture was allowed to warm to room temperature with continual stirring and then to stand overnight.

The mixture was poured on to ice and a brown aqueous solution formed which was extracted with petroleum ether (b.p. 40°–60° C.) and diethyl ether and the aqueous phase retained. The extracts were washed with water and the combined water washing and aqueous phase were acidified to pH 6. The aqueous phase was evaporated at reduced pressure to yield a brown oil which was dried by azeotroping with isopropanol. The dried residue was extracted with hot isopropanol/acetone leaving insoluble inorganic solids which were removed by filtration through diatomaceous earth and washed with more isopropanol/acetone. The combined filtrate and washings were suspended in water which was taken to pH 8 with aqueous sodium bicarbonate solution. The aqueous phase was extracted with ethyl acetate. The extract was washed with water dried (MgSO$_4$) and evaporated at reduced pressure to yield ethyl 2-formyl-3-(3-dimethylaminomethylphenyl)propionate (20.04 g) as a light brown oil.

(v) Nitroguanidine (10.56 g containing 25% w/w water) was washed with methanol (10 ml) into a solution of sodium methoxide in methanol (from 2.62 g sodium and 50 ml methanol). The mixture was stirred under reflux for 0.75 hr and then a solution of 2-formyl-3-(3-dimethylaminomethylphenyl)propionate (20.04 g) in methanol (50 ml) was added dropwise with stirring over 1 hr. This mixture was stirred while being heated under reflux for 22 hr.

The methanol was evaporated at reduced pressure and the residue dissolved in water (100 ml) extracted with chloroform and the chloroform extracts washed with water. The aqueous phase was acidified to pH 5 with glacial acetic acid. An oil precipitated which on being chilled allowed to stand solidified to yield 2-nitroamino-5-(3-dimethylaminomethylbenzyl)-4-pyrimidone (8.79 g) as a pale cream solid m.p. 232°–5° C.

Evaporation of the mother liquor gave an oily residue which when washed with water and boiled with isopropanol solidified to yield a further amount (1.57 g) of the pale cream solid product m.p. 225°–6° C.

(vi) A mixture of 2-(5-methyl-4-imidazolylmethylthio)ethylamine (1.37 g) and 2-nitroamino-5-(3-dimethylaminomethylbenzyl)-4-pyrimidone (2.27 g) in pyridine (12 ml) was refluxed for 18 hr. The solvent was evaporated at reduced pressure the residue washed with water by decantation dried and reacted with maleic acid in acetone. The solvent was evaporated and the residue of 2-[5-methyl-4-imidazolylmethylthio)ethylamino]-5-(3-dimethylaminomethylbenzyl)-4-pyrimidone was recrystallised from isopropanolmethanol to yield the trimaleate (3.07 g) as a light buff solid m.p. 140.5°–142.5° C.

EXAMPLE 13

A mixture of 2-(5-dimethylaminomethyl-2-furanylmethylthio)ethylamine (1.71 g) and 2-nitroamino-5-(3- dimethylaminomethylbenzyl)-4-pyridine (1.97 g) in pyridine (12 ml) was refluxed for 23 hr. The excess of pyridine was then evaporated yielding 2-[2-(5-dimethyl aminomethyl-2-furanylmethylthio)ethylamino]-5-(3-dimethylaminobenzyl)pyrimidone as an oily residue which was washed with water by decantation.

The residue was then dissolved in dilute ethanolic hydrochloric acid and the excess of solvent removed. The residue was recrystallized from isopropanol/ethanol and then from ethanol to yield the trihydrochloride (2.51 g) as a light-buff solid m.p. 182.5° to 185° C.

EXAMPLE 14

(i) A mixture of diethylsulphate (57.41 g) and tri-n-propylamine was added dropwise with stirring to a solution of furanylacrylic acid (34.53 g) in acetone (150 ml). When the addition was complete the mixture was refluxed for six hours. The acetone was evaporated at reduced pressure. The resultant oily residue was dissolved in ethyl acetate, washed with aqueous sodium bicarbonate solution dried (MgSO$_4$) and the solvent evaporated to yield ethyl 3-(2-furanyl)acrylate (46.7 g) as a brown oil.

(ii) A mixture of ethyl 3-(2-furanyl)acrylate (46.7 g) and conc. ammonium hydroxide solution (25 ml) was hydrogenated in the presence of Raney Nickel (500 mg) at 35° C. until a theoretical amount of hydrogen was taken up. The Raney Nickel was removed by filtering through diatomaceous earth and the filtrate was evaporated at reduced pressure to yield a brown oil. The oil was dissolved in ethyl acetate, washed with distilled water, dried (MgSO$_4$) and the solvent evaporated at reduced pressure to yield ethyl 3-(2-furanyl)-propionate (33.77 g) as a brown oil.

(iii) A mixture of ethyl 3-(2-furanyl)propionate (33.77 g) and ethyl formate (22.22 g) was added dropwise with stirring to a pre-cooled (0° C.) suspension of sodium hydride (50% in oil; 8.45 g) in dimethoxyethane (70 ml) maintaining the temperature below 0° C. throughout the addition. The reaction mixture was allowed to warm to room temperature then poured on to ice and water and extracted with ethyl acetate. The aqueous layer was acidified to pH 4 and re-extracted with ethyl acetate. These second ethyl acetate extracts were combined dried (MgSO$_4$) and evaporated at reduced pressure to yield ethyl 3-(2-furanyl)-2-formylpropionate (19.0 g).

(iv) Nitroguanidine (12.59 g containing 25% w/w water) was added to a solution of sodium methoxide in methanol (from 6.25 g sodium and 100 ml methanol) and the mixture was refluxed until solution was complete. The mixture was cooled and ethyl 3-(2-furanyl)-2-formylpropinate (19g) was added. This mixture was then refluxed for ca 16 hr. The methanol was evaporated at reduced pressure yielding an oil which was mixed with water and acidified to pH 4 with glacial acetic acid. Cooling and trituration of the aqueous mixture yielded a solid which was recrystallised from glacial acetic acid yielding 2-nitroamino-5-(2-furanylmethyl)-4-pyrimidone (6.48 g) m.p. 183°–4° C.

Evaporation of the mother liquors yields a further amount (2.49 g) of product, m.p. 181°–2° C.

(v) A solution of 2-nitroamino-5-(2-furanylmethyl)-4-pyrimidone (5.24 g) in ethanol (50 ml) was added to a solution of 2-[2-(2-furanyl)methylthio]ethylamine (3.49 g). The mixture was refluxed for 24 hr. Reaction was stopped and the ethanol evaporated to leave an oil which was dissolved in ethyl acetate containing a trace of methanol and the resulting solution was extracted with distilled water. The aqueous phase was back extracted with ethyl acetate. The ethyl acetate extracts were combined extracted with distilled water, dried (MgSO$_4$), and evaporated to dryness to give an oil (4.74 g). The oil was chromatographed on a silica-gel column using initially petroleum ether 40°–60° C., ethyl acetate (80%, 20%), and then petroleum ether 40°–60° C., ethyl acetate (60%, 40%). The eluate containing the required product was evaporated to dryness to give an oil (3.36 g) which was dissolved in ethyl acetate, and chromatographed on a silica-gel column eluting with ethyl acetate. The eluate containing the product was evaporated to dryness to give 2-[2-(2-furanyl)methylthio]ethylamino]-5-(2-furanyl)-4-pyrimidone as an oil (2.28 g) which was dried over P$_2$O$_5$ under vacuum.

(vi) Bis-dimethylaminomethane (1.23 g,) was added whilst stirring 2-[2-(2-furanylmethylthio)ethylamino]-5-(2-furanylmethyl)-4-pyrimidone (0.8 g) was suspended in glacial acetic acid (8 ml). The mixture was then stirred at room temperature for 3 hr and allowed to stand for ca 16 hr. The acid was evaporated at reduced pressure azeotropically with water. The residual oil was dissolved in water, filtered and the filtrate taken to pH 9 using aqueous sodium carbonate solution. The basic solution was extracted using ethyl acetate, the extracts dried (MgSO$_4$) and evaporated to give 2-[2-(5-dimethylaminomethyl-2-furanylmethylthio)ethylamino]-5-(5-dimethylaminomethyl-2-furanylmethyl)-4-pyrimidone as an oily residue (1.01 g). The oily residue was dissolved in a minimum volume of ethanol and then acidified with ethanolic hydrochloric acid. The acidic solution was then evaporated to dryness and the residual oil was crystallised from isopropanol/ethanol to give the white solid trihydrochloride salt (1.33 g) m.p. 177°–9° C.

EXAMPLE 15

(i) 2-Hydroxymethyl-4-cyanopyridine (6.71 g) was added portionwise over 15 min to thionyl chloride (24.6 g) which was being stirred. The stirring was continued for min. The excess of thionyl chloride was evaporated at reduced pressure to yield a solid residue to which was added diethyl ether (15 ml). This mixture was cooled (to ca 0° C.) and to it was added a solution of dry dimethylamine (15 ml) in dry diethyl ether (15 ml) dropwise over 10 min. This new mixture was stirred for 30 min and allowed to stand (for ca 16 hr).

The mixture was washed with water and the water washings were extracted with ether and ethyl acetate. The organic phases were combined, dried (MgSO$_4$) and the solvent evaporated to give 4-cyano-2-dimethylaminomethyl pyridine (8.02 g) as a straw coloured oil.

(ii) 4-Cyano-2-dimethylaminomethyl pyridine is converted into 2-nitroamino-5-(2-dimethylaminomethyl-4-pyridylmethyl)-4-pyrimidone by the method of Example 12 (i) to (v).

(iii) Reaction of 2-nitroamino-5-(2-dimethylaminomethyl-4-pyrimidone with 2-(5-methyl-4-imidazolylmethylthio)ethylamine by the method of Example 12 (vi) gives 2-[2-(5-methyl-4-imidazolylmethylthio)ethylamino]-5-(2-dimethylaminomethyl-4-pyridylmethyl)-4-pyrimidone.

EXAMPLE 16

Reaction of 3-(3-dimethylaminomethylphenoxy)-propylamine with 2-nitroamino-5-(5-dimethylaminomethyl-2-thienyl methyl)-4-pyrimidone gives 2-[3-(3-dimethylaminomethylphenoxy)propylamino]-5-(5-dimethylaminomethyl-2-thienylmethyl)-4-pyrimidone.

EXAMPLE 17

Reaction 4-(3-methylpyridyl)butylamine with 2-nitroamino-5-(5-dimethylaminomethyl-3-pyridylmethyl)-4-pyrimidone gives 2-[4-(3-methylpyridyl)-butylamino]-5-(5-dimethylaminomethyl-3-pyridylmethyl)-4-pyrimidone.

EXAMPLE 18

Reaction of 2-(2-thiazolylmethylthio)ethylamine with 2-nitroamino-5-dimethylaminomethyl-2-thienylmethyl)-4-pyrimidone gives 2-[2-(2-thiazolylmethylthio)ethylamino]-(5-dimethylaminomethyl-2-thienylmethyl)-4-pyrimidone.

EXAMPLE 19

(i) Reaction of 4-(3-methoxypyridyl)butylamine with 2-nitroamino-5-(5-di-n-butylaminomethyl-2-thienylmethyl)-4-pyrimidone gives 2-[4-(3-methoxypyridyl)-butylamino]-5-(5-di-n-butylaminomethyl-2-thienylmethyl)-4-pyrimidone.

(ii) Reaction of 4-(3-methoxypyridyl)butylamine with 2-nitroamino-5-(4-dimethylaminomethyl-2-pyridylmethyl)-6-methyl-4-pyrimidone gives 2-[4-(3-methoxypyridyl)butyl-amino]-5-(4-dimethylaminomethyl-2-pyridylmethyl)-6-methyl-4-pyrimidone.

(iii) Reaction of 2-(5-dimethylaminomethyl-2-furanylmethylthio)ethyl amine with 2-nitroamino-5-(5-dimethylaminomethyl-2-pyridylmethyl)-6-methyl-4-pyrimidone gives 2-[2-(5-dimethylaminomethyl-2-furanylmethylthio)ethylamino]-5-(5-dimethylaminomethyl-2-pyridylmethyl)-6-methyl-4-pyrimidone.

EXAMPLE 20

Reaction of 2-(5-(1-pyrrolidinomethyl)-2-thienylmethylthio)ethylamine with 2-nitroamino-5-[5-(1-piperidinomethyl)-2-thienylmethyl]-4-pyrimidone gives 2-[2-(5-(1-pyrrolidinomethyl)-2-thienylmethylthio)ethylamino]-5-(1-piperidinomethyl)-[2-thienylmethyl]-4-pyrimidone.

EXAMPLE 21

(i) Reaction of 2-(5-(3-(1-morpholino)butyl)-2-thienylmethylthio)ethyl amine with 2-nitroamino-5-[5-(1-piperidinomethyl)2-thienylmethyl]-4-pyrimidone gives 2-[2-(5-(3-(1-morpholinobutyl)-2-thienylmethylthio)ethylamino]-5-[5-(1-piuperidinomethyl)-2-thienylmethyl]-4-pyrimidone.

EXAMPLE 22

A pharmaceutical composition for oral administration is prepared containing:

| | | % W/W |
|---|---|---|
| A | 2-[2-(5-dimethylamino-2-furanylmethylthio)-ethylamino]-5-(5-dimethylaminomethyl-2-furanylmethyl-4-pyrimidone trihydrochloride. | 55 |
| | Dibasic calcium phosphate dihydrate. | 20 |
| | Approved Colouring Agent. | 0.5 |
| | Polyvinylpyrrolidone | 4.0 |
| | Microcrystalline Cellulose | 8.0 |
| B | Maize Starch | 8.0 |
| | Sodium glycollate | 4.0 |
| | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets, containing 100 mg, 150 mg or 200 mg of the free base.

EXAMPLE 23

A pharmaceutical composition for oral administration is prepared containing:

| | | % W/W |
|---|---|---|
| A | 2-[2-(5-dimethylamino-2-furanylmethylthio)-ethylamino]-5-(2-dimethylaminomethyl-4-pyridylmethyl-4-pyrimidone trihydrochloride. | 55 |
| | Dibasic calcium phosphate dihydrate. | 20 |
| | Approved Colouring Agent. | 0.5 |
| | Polyvinylpyrrolidone | 4.0 |
| | Microcrystalline Cellulose | 8.0 |
| B | Maize Starch | 8.0 |
| | Sodium glycollate | 4.0 |
| | Magnesium Stearate | 0.5 |

This composition is made by the process described in Example 22.

EXAMPLE 24

A pharmaceutical composition for oral administration is prepared containing:

| | | % W/W |
|---|---|---|
| A | 2-[2-(5-dimethylamino-2-furanylmethylthio)-ethylamino]-5-(2-dimethylaminomethyl-3-pyridylmethyl-4-pyrimidone trihydrochloride. | 55 |
| | Dibasic calcium phosphate dihydrate. | 20 |
| | Approved Colouring Agent. | 0.5 |
| | Polyvinylpyrrolidone | 4.0 |
| | Microcrystalline Cellulose | 8.0 |
| B | Maize Starch | 8.0 |
| | Sodium glycollate | 4.0 |
| | Magnesium Stearate | 0.5 |

This composition is made by the process described in Example 22.

EXAMPLE 25

A pharmaceutical composition for topical application is prepared containing:

| | | % W/W | |
|---|---|---|---|
| A | Stearyl alcohol | 15.0 | |
| | Beeswax | 8.0 | |
| | Sorbitan mono-oleate | 1.25 | |
| | Polyoxyethylene sorbitan mono-oleate | 3.75 | |
| | Sorbitol solution B.P. | 7.5 | |
| B | Citric Acid | 0.2 | |
| | Sodium citrate | 0.05 | |
| | Methylparaben | 0.18 | |
| | Propylparaben | 0.02 | |
| | Water | to | 100 |

A mixture of the ingredients A is heated to 72° C. and added with stirring to a mixture of the ingredients B at 70° C., and the stirring is continued until a cream is formed.

We claim:

1. A compound of formula (I):

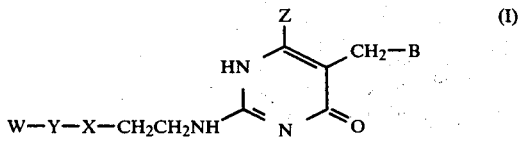

where
- W is a 2-furanyl or 2-thienyl group optionally substituted in the 5-position with a group $R^1R^2N(CH_2)_m$—; a phenyl group substituted in the 3- or 4-position with a group $R^1R^2N(CH_2)_m$—; a 4-imidazolyl group optionally substituted in the 5-position with methyl or bromine; a 2-pyridyl group optionally substituted in the 3-position with $C_{1-4}$ alkyl, $C_{1-4}$ alkoxy, halogen, amino or hydroxy; a 2-thiazolyl group or a 2-guanidino-4-thiazolyl group;
- X is methylene or sulphur
- and Y is methylene or, provided X is methylene and W is a substituted phenyl group, oxygen;
- Z is hydrogen or $C_{1-4}$ alkyl;
- and B is a 2-furanyl or 2-thienyl group substituted in the 5-position by a group $R^1R^2N(CH_2)_m$—; a phenyl group substituted in the 3- or 4-position by a group $R^1R^2N(CH_2)_m$— or a 3-pyridyl group substituted in position 5 or 6 or a 4-pyridyl group substituted in position 2 by a group $R^1R^2N(CH_2)_m$;
- $R^1$ and $R^2$ are $C_{1-4}$ alkyl or together with the nitrogen atom to which they are attached form a pyrrolidino, piperidino or morpholino group;
- m is 1 to 4;

or a pharmaceutically acceptable acid addition salt thereof.

2. A compound according to claim 1 where Z is hydrogen.

3. A compound according to claim 1 where in the group B, $R^1$ and $R^2$ are both methyl and m is 1.

4. A compound according to claim 3 where B is 5-dimethylaminomethyl-2-furanyl, 6-dimethylaminomethyl-3-pyridyl or 2-dimethylaminomethyl-4-pyridyl.

5. A compound according to claim 4 where W is phenyl substituted in the 3- or 4-position with $R^1R^2N(CH_2)_m$—.

6. A compound according to claim 5 where Y is oxygen, X is methylene and group $R^1R^2N(CH_2)_m$— is in the 3-position.

7. A compound according to claim 1 where W is 2-furanyl or 2-thienyl optionally substituted in the 5-position with $R^1R^2N(CH_2)_m$—; 4-imidazolyl optionally substituted in the 5-position with methyl or bromine; 2-pyridyl optionally substituted in the 3-position with $C_{1-4}$ alkyl, $C_{1-4}$ alkoxy, halogen, amino or hydroxy; 2-thiazolyl or 2-guanidino-4-thiazolyl.

8. A compound according to claim 7 where W is a 2-furanyl or 2-thienyl group optionally substituted in the 5-position with the group $R^1R^2N(CH_2)_m$—; a 4-imidazolyl group optionally substituted in the 5-position with methyl or bromine; a 2-thiazolyl group or a 2-guanidino-4-thiazolyl group.

9. A compound according to claim 7 where Y is methylene and X is sulphur.

10. A compound according to claim 9 where W is 2-furanyl or 2-thienyl substituted in the 5-position with the group $R^1R^2N(CH_2)_m$— where $R^1$ and $R^2$ are both methyl and m is 1.

11. A compound according to claim 10 where W is 5-dimethylaminomethyl-2-furanyl.

12. A compound according to claim 1 where B and W are the same and represent 2-furanyl or 2-thienyl substituted in the 5-position with a group $R^1R^2N(CH_2)_m$— and m is 1.

13. A compound according to claim 4 which is 2-[2-(5-methyl-4-imidazolylmethylthio)ethylamino]-5-(5-dimethylaminomethyl-2-furanylmethyl)-4-pyrimidone or a pharmaceutically acceptable acid addition salt thereof.

14. A compound according to claim 4 which is 2-[2-(2-guanidino-4-thiazolylmethylthio)ethylamino]-5-(5-dimethylaminomethyl-2-furanylmethyl)-4-pyrimidone, or a pharmaceutically acceptable acid addition salt thereof.

15. A compound according to claim 4 which is 2-[3-(3-dimethylaminomethylphenoxy)propylamino]-5-(5-dimethylaminomethyl-2-furanylmethyl)-4-pyrimidone or a pharmaceutically acceptable acid addition salt thereof.

16. A compound according to claim 4 which is 2-[2-(5-methyl-4-imidazolylmethylthio)ethylamino]-5-(6-dimethylaminomethyl-3-pyridylmethyl)-4-pyrimidone or a pharmaceutically acceptable acid addition salt thereof.

17. A compound according to claim 9 which is 2-[2-(5-dimethylaminomethyl-2-furanylmethylthio)ethylamino]-5-(5-dimethylaminomethyl-2-thienylmethyl)-4-pyrimidone or a pharmaceutically acceptable acid addition salt thereof.

18. A compound according to claim 9 which is 2-[2-(5-dimethylaminomethyl-2-furanylmethylthio)ethylamino]-5-(3-dimethylaminomethylbenzyl)-4-pyrimidone, or a pharmaceutically acceptable acid addition salt thereof.

19. A compound according to claim 9 which is 2-[2-(5-dimethylaminomethyl-2-furanylmethylthio)ethylamino]-5-(5-dimethylaminomethyl-2-furanylmethyl)-4-pyrimidone or a pharmaceutically acceptable acid addition salt thereof.

20. A compound according to claim 9 which is 2-[2-(5-dimethylaminomethyl-2-furanylmethylthio)ethylamino]-5-(2-dimethylaminomethyl-4-pyridylmethyl)-4-pyrimidone or a pharmaceutically acceptable acid addition salt thereof.

21. A compound according to claim 9 which is 2-[2-(5-dimethylaminomethyl-2-furanylmethylthio)ethylamino]-5-(6-dimethylaminomethyl-3-pyridylmethyl)-4-pyrimidone or a pharmaceutically acceptable acid addition salt thereof.

22. A hydrochloric, hydrobromic, sulphuric, phosphoric, acetic, citric or maleic acid salt of a compound of formula (I) according to claim 1.

23. A compound according to claim 16 which is 2-[2-(5-methyl-4-imidazolylmethylthio)ethylamino]-5-(6-dimethylaminomethyl-3-pyridylmethyl)-4-pyrimidone tetrahydrochloride.

24. A compound according to claim 17 which is 2-[2-(5-dimethylaminomethyl-2-furanylmethylthio)ethylamino)-5-(5-dimethylaminomethyl-2-thienylmethyl)-4-pyrimidone trihydrochloride.

25. A compound according to claim 18 which is 2-[2-(5-dimethylaminomethyl-2-furanylmethylthio)ethylamino]-5-(3-dimethylaminomethylbenzyl)-4-pyrimidone, trihydrochloride.

26. A compound according to claim 19 which is 2-[2-(5-dimethylaminomethyl-2-furanylmethylthio)ethylamino]-5-(5-dimethylaminomethyl-2-furanylmethyl)-4-pyrimidone trihydrochloride.

27. A compound according to claim 20 which is 2-[2-(5-dimethylaminomethyl-2-furanylmethylthio)ethylamino]-5-(2-dimethylaminomethyl-4-pyridylmethyl)-4-pyrimidone trihydrochloride.

28. A compound according to claim 21 which is 2-[2-(5-dimethylaminomethyl-2-furanylmethylthio)ethylamino]-5-(6-dimethylaminomethyl-3-pyridylmethyl)-4-pyrimidone 3.8 hydrochloride 1.4 hydrate.

29. A pharmaceutical composition having histamine $H_2$-receptor blocking activity comprising in an amount effective to block said receptors, a compound of claim 1 and a pharmaceutically acceptable carrier.

30. A method of blocking histamine $H_2$-receptors which comprises administering to an animal an effective amount to block said receptors of a compound of claim 1 or a pharmaceutically acceptable acid addition salt thereof.

* * * * *

UNITED STATES PATENT AND TRADEMARK OFFICE
CERTIFICATE OF CORRECTION

PATENT NO. : 4,388,317

DATED : June 14, 1983

INVENTOR(S) : Thomas H. Brown

It is certified that error appears in the above-identified patent and that said Letters Patent is hereby corrected as shown below:

On the title page, insert the following:

-- [30]    Foreign Application Priority Data

March 29, 1980    United Kingdom 8010663
    January 21, 1981   United Kingdom 8101705 --.

Signed and Sealed this

Twenty-third Day of August 1983

[SEAL]

Attest:

GERALD J. MOSSINGHOFF

Attesting Officer    Commissioner of Patents and Trademarks